United States Patent [19]
Umezawa et al.

[11] 3,992,524
[45] Nov. 16, 1976

[54] ANTITUMOR ANTIBIOTIC MACRACIDMYCIN

[75] Inventors: Hamao Umezawa; Tomio Takeuchi, both of Tokyo; Masa Hamada, Hoya; Masaaki Ishizuka, Tokyo; Akira Takamatsu, Yokohama; Toshikazu Oki, Kamakura; Hiroshi Tone, Fujisawa, all of Japan

[73] Assignee: Zaidan Hojin Biseibutsu Kagaku Kenkyu Kai, Tokyo, Japan

[22] Filed: Mar. 3, 1975

[21] Appl. No.: 555,011

[30] Foreign Application Priority Data
Mar. 29, 1974 Japan.............................. 49-34626

[52] U.S. Cl. .............................. 424/115; 195/80 R
[51] Int. Cl.$^2$......................................... A61K 35/74
[58] Field of Search.................... 424/115; 195/80 R

[56] References Cited
OTHER PUBLICATIONS

Suhava et al., J. Antibiotics, Ser. A16, 1963, pp. 107–108.

Murase et al., J. Antibiotics, Ser. A14, 1961, pp. 113–118.

Nakamura et al., J. Antibiotics, Ser. A20, 1967, pp. 210–216.

Ishida et al., J. Antibiotics, 22, 1969, pp. 218–227.

*Primary Examiner*—Jerome D. Goldberg
*Attorney, Agent, or Firm*—Herbert W. Taylor, Jr.

[57] ABSTRACT

A new antitumor agent named macracidmycin, which is a macromolecular peptide and inhibits the growth of various tumor cells and experimental animal tumors such as Ehrlich ascites carcinoma and Sarcoma 180 is produced by the fermentation of a microorganism belonging to the genus Streptomyces which has been designated *Streptomyces atrofaciens* (M590-G2 and A.T.C.C. 31104); it is recovered from the broth by conventional methods for recovering antibiotics.

9 Claims, 2 Drawing Figures

INFRARED ABSORPTION SPECTRUM OF MACRACIDMYCIN IN KBr

ANTITUMOR ANTIBIOTIC MACRACIDMYCIN

BACKGROUND OF THE INVENTION

1. Field of the Invention

This invention relates to a new antitumor antibiotic substance and to its production. More particularly, it relates to a new antitumor antibiotic substance designated macracidmycin and to processes for the preparation thereof by the fermentation of a strain of *Streptomyces atrofaciens* (e.g., M590-G2) and to methods for its recovery and purification.

2. Description of the Prior Art

Hamao Umezawa, one of the inventors of the present invention has studied antitumor antibiotics produced by Streptomyces since 1951 and in 1965 he emphasized the importance of antitumor antibiotics with a macromolecular nature as described in his paper "Bleomycin and Other Antitumor Antibiotics of High Molecular Weight", Antimicrobial Agents and Chemotherapy, 1965, pages 1079–1085. In the continuation of the study of the macromolecular antitumor antibiotics, the present inventors discovered a new compound and after characterization and purification based on its physicochemical properties, they confirmed that this antibiotic now named macracidmycin is a new compound which shows a new type of activity in interacting cell membrane, and they established processes and methods for its production and isolation.

SUMMARY OF THE INVENTION

There is provided by the present invention the antitumor agent macracidmycin. The substance is produced by cultivating a macracidmycin-producing strain of *Streptomyces atrofaciens* in an aqueous carbohydrate solution containing an organic nitrogenous nutrient under submerged aerobic conditions until a substantial quantity of macracidmycin is formed in said solution. Macracidmycin in cultured broths thus prepared can be extracted and purified by conventional methods used for extraction and purification of protein. This invention also embraces macracidmycin in dilute solution, as crude concentrates, as crude solids and as purified solids.

There is thus provided by the present invention the antitumor antibiotic macracidmycin which:

a. is effective in inhibiting the growth of ascites forms of Ehrlich carcinoma and Sarcoma 180 in mice, and vaccinia virus in HeLa cells;

b. can be isolated as a white amorphous powder;

c. is soluble in water but substantially insoluble in organic solvents;

d. exhibits an ultraviolet absorption maximum at 280 microns in aqueous solution;

e. exhibits characteristic maxima in the infrared absorption spectrum at 3320, 3075, 2940, 1645, 1540, 1460, 1420, 1230 and 1070 cm$^{-1}$;

f. gives positive Folin-Lowry, ninhydrin, Sakaguchi, and biuret reactions and negative Elson-Morgan and anthrone reactions;

g. has an isoelectric point of pH 6.0;

h. is a weakly acidic polypeptide having a high molecular weight for which a molecular weight of 35,000 to 38,000 is indicated by gel filtration; and i. gives upon acid hydrolysis the following amino acids (molar ratio): Aspartic acid (8), threonine (7), serine (8), glutamic acid (7), proline (2), glycine (16), alanine (10), valine (4), leucine (4), isoleucine (2), tyrosine (2), phenylalanine (2), histidine (1), lysine (3), arginine (2), ammonia (16) and an unknown amino acid between histidine and lysine on an amino acid analyzer.

There is further provided by the present invention the process for producing the antitumor antibiotic macracidmycin which comprises culturing a macracidmycin-producing strain of *Streptomyces atrofaciens* having the identifying characteristics of A.T.C.C. 31104 under submerged aerobic conditions in a nutrient medium containing a carbon source and a nitrogenous nutrient until a substantial amount of macracidmycin is produced by said oroganism in said nutrient medium and preferably is cultured in a nutrient medium at a temperature in the range of 24° to 35° C. or better yet at a temperature in the range of 25° to 29° C. with the pH from 6 to 8 and then, if desired, recovering the macracidmycin from the culture medium by a process which includes at least one process selected from the group consisting of salting-out, solvent precipitation, dialysis, ultrafiltration, isoelectric precipitation, gel filtration, electrophoresis, electrofocusing and adsorption followed by elution from an ion exchange resin.

The processes of this invention include a process in which the solution containing macracidmycin is stored in a cold or frozen state and a process in which the solution containing macracidmycin is freeze-dried and a process in which the solution containing macracidmycin is freeze-dried after addition of at least one stabilizer selected from the group consisting of serum serum albumin, serum globulin, casein, glycerol, gelatin, sugars and amino acids.

DETAILED DESCRIPTION

Macracidmycin inhibits the proliferation of HeLa cells, leukemia L1210 and murine leukemia L5178Y cells in culture and prolongs the lives and improves the condition of mice inoculated with Sarcoma 180 and Ehrlich carcinoma. More particularly, the substance caused the rapid swelling and lysis of cells in a short period of contact with the various tumor cells but has no antimicrobial activity against bacteria, fungi, yeast and mycoplasmas.

Figure 2:
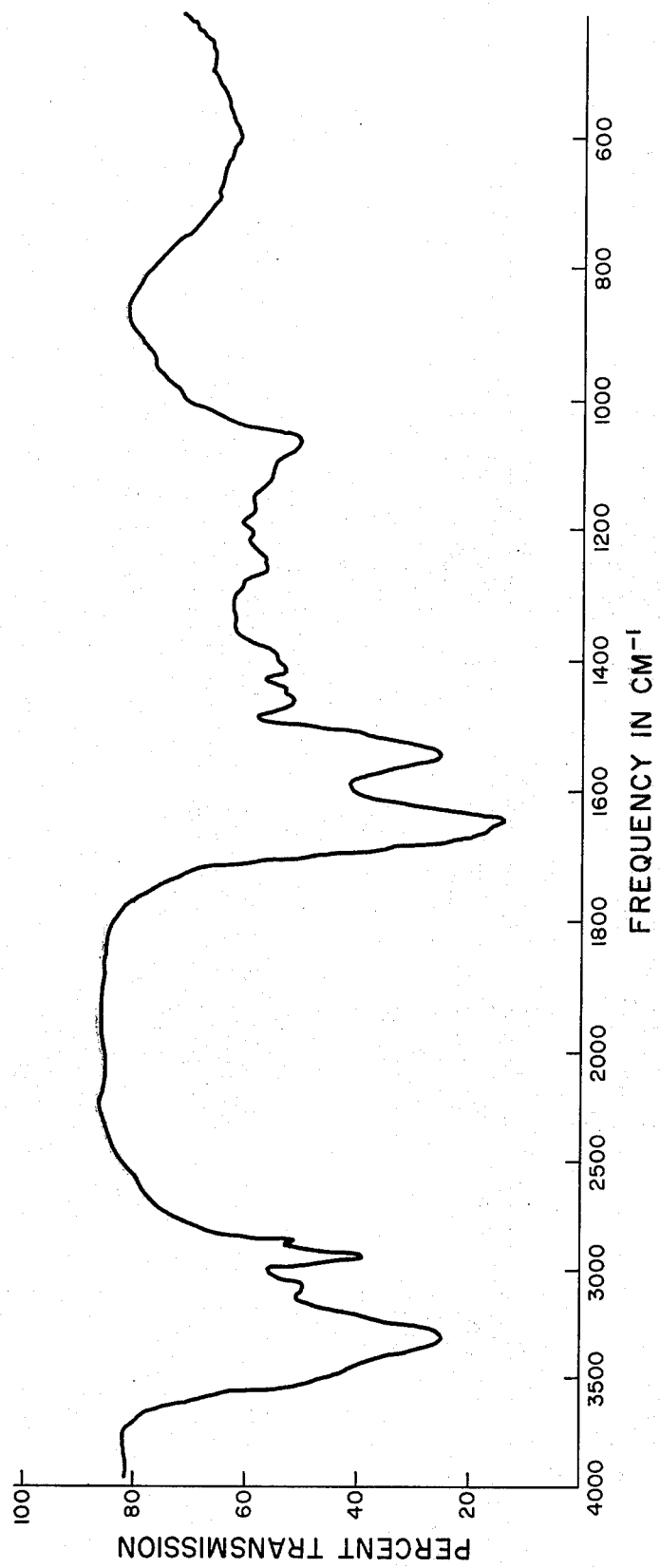
FIG. 2 is the infrared absorption spectrum of macracidmycin in potassium bromide.

Macracidmycin is obtained as a white powder which has a molecular weight of approximately 35,000 to 38,000, said substance being soluble in water but not in organic solvents, exhibiting an absorption maximum of ultraviolet light at 280 microns in aqueous solution, having an infrared absorption spectrum substantially as shown in FIG. 2 and exhibiting characteristic absorption maxima in the infrared region when pelleted with potassium bromide at the following wave numbers in cm$^{-1}$: 3320, 3075, 2940, 1645, 1540, 1460, 1420, 1230 and 1070, giving a positive ninhydrin reaction, having an isoelectric point of pH 6.0, and being a weakly acidic polypeptide of which the hydrolysate contains 16 amino acids.

There is further provided according to the present invention the process for the production of the antitumor antibiotic macracidmycin which comprises cultivating a strain of *Streptomyces atrofaciens* M590-G2 in an aqueous medium containing carbon sources and nitrogen sources under aerobic conditions until a substantial amount of macracidmycin is accumulated in said solution, and then recovering said macracidmycin from said solution using the methods of salting-out, adsorption to ion exchanger, dialysis, solvent precipitation, gel-filtration, ultra-filtration, etc. and combinations of these methods.

Although a number of high molecular weight antitumor substances are known, e.g. melanomycin, actinogan, peptimycin, enomycin, malinamycin, carzinostatin, neocarzinostatin, largomycin, macromomycin, etc., macracidmycin as produced by the process of this invention is clearly different from any of them in the characteristics of molecular weight, antimicrobial effects, amino acid composition, isoelectric point and the like, as described above. Moreover, its remarkably high chemotherapeutic properties and the rapid swelling and lysis of tumor cells exposed for short period to a low concentration of macracidmycin are characteristics not exhibited by any of the conventional antitumor substances.

The organism producing the antibiotic macracidmycin of the present invention was isolated from a soil sample collected at Soshigaya, Setagaya-ku, Tokyo, Japan and is a strain of the species *Streptomyces atrofaciens* which has been given the laboratory designation M590-G2 in our laboratory. A culture of M590-G2 was deposited in the American Type Culture Collection, Rockville, Maryland and the Fermentation Research Institute, Japan, and added to their permanent collections of microorganisms as A.T.C.C. No. 31104 and FERM No. 2454, respectively.

The strain No. M590-G2 has the following characteristics:

1. Morphological characteristics:

Under the microscope, the long straight aerial hyphae (rectiflexibilis) are observed to develop well from fine branched substrate mycelia on inorganic salts-starch agar. Aerial hyphae form neither whorls nor spirals. Mature spore chain is long and bore more than ten spores per chain. The spores are ellipsoidal and measured $0.8-1.0 \times 1.0-1.2\mu$, and its surface is smooth under electron microscope.

2. Characteristics on various media:

The description in parenthesis follows the color standard "Color Harmony Manual" published by Container Corporation of America, U.S.A.

a. On sucrose-nitrate agar, incubated at 27° C: Colorless growth; grayish white aerial mycelium slightly; no soluble pigment.

b. On glucose-aspargine agar, incubated at 27° C: Brownish gray growth; pinkish white mycelium; light yellowish brown soluble pigment.

c. On glycerol-aspargine agar (ISP medium No. 5), incubated at 27° C: Dark brownish gray growth (41 g., toast tan); white to brownish white aerial mycelium; brownish soluble pigment.

d. On starch-inorganic salts agar, incubated at 27° C: Light brown (41 g., toast tan) to yellowish brown (3ni, clove brown) growth; pinkish white (5ba, shell pink) to pinkish gray (5cb) aerial mycelium; light yellow soluble pigment.

e. On tyrosine agar, incubated at 27° C: Abundant grayish brown to dark brown (4ul, dark brown) growth; pinkish white (5ba, shell pink) to brownish white (3dc, natural) aerial mycelium; dark brownish gray to brownish black soluble pigment; tyrosinase reaction is positive.

f. On nutrient agar, incubated at 27° C: Light brownish gray growth; light gray aerial mycelium; dark brown soluble pigment.

g. On yeast extract-malt extract agar, incubated at 27° C: Abundant brown (4ni, spice brown to 4pl, deep brown) growth; pinkish white (5ba, shell pink) to pinkish gray (5cb) aerial mycelium; brown soluble pigment.

h. On oatmeal agar (ISP medium No. 3), incubated at 27° C: Light brown growth (4ge, rose beige); white pink to pinkish gray(4ca, shell pink) aerial mycelium; slight yellow soluble pigment.

i. On starch plate, incubated at 27° C: Dark yellowish brown to brownish black growth; white to pinkish white aerial mycelium; light yellowish brown soluble pigment.

j. On calcium malate agar, incubated at 27° C: Colorless growth; white aerial mycelium; no soluble pigment.

k. On gelatin stab, incubated at 20° C: Poor and colorless to pale yellowish brown growth; white aerial mycelium; dark yellowish brown soluble pigment.

l. On glucose-peptone-gelatin stab, incubated at 27° C: COlorless to light brown growth; gray to brownish gray aerial mycelium; greenish gray to brown soluble pigment.

m. On skimmed milk, incubated at 37° C: Brown growth; no aerial mycelium; brown soluble pigment.

n. On potato plug, incubated at 27° C: Poor and brownish black growth; white to brownish white aerial mycelium; brownish black soluble pigment.

o. On cellulose, incubated at 27° C: Colorless to brownish black growth; no aerial mycelium; black soluble pigment.

p. On Loeffler's coagulated serum medium, incubated at 37° C: Thin, dry and dark brownish gray growth; no aerial mycelium; dark brownish gray soluble pigment.

3. Physiological characteristics:

a. Growth temperature on glucose-asparagine agar: Optimal temperature for the growth is 27° C. to 30° C., and no growth above 50° C.

b. Gelatin liquefaction on 15% gelatin stab at 20° C. and on glucose-peptone-gelatin stab at 27° C: Negative.

c. Starch hydrolysis on starch-inorganic salts agar and starch agar at 27° C: Weak or moderate hydrolysis after 10 days incubation.

d. Peptonization and coagulation of skimmed milk at 37° C: Positive.

e. Melanin formation on tyrosine-yeast extract broth (ISP medium No. 1), peptone-yeast extract-$Fe^{++}$ agar (ISP medium No. 6), and tryosine agar (ISP medium No. 7) at 27° C: Positive.

f. Liquefaction of calcium malate at 27° C: Negative.

g. Nitrite formation on peptone water containing 1% sodium nitrate (ISP medium No. 8) at 27° C: Positive.

h. Utilization of carbohydrates of Pridham-Gottlieb basal medium, incubated at 27° C: Abundant growth with glucose, glycerol, L-arabinose, D-mannitol and raffinose; slight growth with D-fructose and inositol; no growth with D-xylose, sucrose and L-rhamnose.

Summarizing the above characteristics of No. M590-G2 the strain belongs to the genus Streptomyces and chromogenic type, and brown to yellowish brown soluble pigment is produced on various agar media. Aerial mycelium forms neither whorls nor spirals. The spore surface is smooth. The growth on various media is found to be light brown to dark yellowish brown in general and the aerial mycelium is pinkish white to pinkish gray or light brownish gray. Nitrate is reduced to nitrite. The proteolytic action and hydrolysis of starch are relatively weak. Melanin is formed on tyrosine agar, tryptone-yeast extract broth, and peptone-yeast extract-$Fe^{++}$ agar.

Among known species of Streptomyces, strain No. M590-G2 resembles *Streptomyces melanogenes* (International Journal of Systematic Bacteriology, 18, 348, 1968 and J. Antibiotics, Ser. A, 10, 138–142, 1957) and *Streptomyces atrofaciens* (International Journal of Systematic Bacteriology, 22, 274, 1972). With particular attention to differentiation based on the morphology, color of the aerial mycelia and other physiological characteristics, the difference between this strain and reference strains *S. melanogenes* ISP 5192 (IFO 12890) and *S. atrofaciens* ISP 5475 (IFO 13395), was investigated. The results are as follows:

Macracidmycin is produced by the cultivation of *S. atrofaciens* under suitable conditions. The general procedures used for the cultivation of other actinomycetes are applicable to the cultivation of *S. atrofaciens*. A fermentation broth containing macracidmycin is prepared by inoculating spores or mycelia of the macracidmycin-producing organism into a suitable medium and then cultivating under aerobic conditions. Although cultivation on a solid medium is possible for the production of macracidmycin, submerged aerobic culture is especially advantageous for production of large quantities of the antibiotic. Media consisting of known kinds of nutritional sources for actinomycetes can be used. The medium preferably contains a source of carbon such as dextrose, starch, glucose, maltose, sucrose, glycerol, molasses, dextrin, oil, fats and the like and, as

|  | M590-G2 | S. melanogenes ISP 5192 | S. atrofaciens ISP 5475 |
|---|---|---|---|
| Spore chain | Rectiflexibiles | Rectiflexibiles | Rectiflexibles |
| Spore surface | smooth | smooth | smooth |
| Aerial mycelium | pinkish white to pinkish gray | pinkish white | pinkish white to pinkish gray |
| Growth | light brown to dark brown | light brown to yellow | yellowish brown to dark brown |
| Soluble pigment | brown | brown | brown |
| Soluble pigment on starch-inorganic salts agar | olive | brown | olive |
| Growth on glucose-asparagine | yellow to brown | light brownish gray | yellowish brown to dark brown |
| Growth on tyrosine agar | yellowish brown | colorless | grayish brown to yellowish brown |
| Melanin formation | positive | positive | positive |
| Hydrolysis of starch | positive, weak to moderate | positive, strong | positive, weak to moderate |
| Coagulation of milk | weak | strong | weak |
| Peptonization of milk | weak | strong | weak |
| Liquefaction of gelatin | negative | negative (positive)* | negative |
| Liquefaction calcium malate | negative | strongly positive | negative |
| Utilization of carbohydrates: |  |  |  |
| D-Xylose | negative | probably positive | probably negative |
| D-Fructose | positive | positive | probably negative |
| Sucrose | negative | negative | negative |
| D-Mannitol | positive | positive | negative |
| Inositol | positive | positive | probably positive |

*( ) from reference

From the results, the present strain is very similar to *S. melanogenes* and *S. atrofaciens*. Although *S. melanogenes* utilizes D-xylose and *S. atrofaciens* does not utilize D-mannitol and D-fructose differentiating it from strain No. M590-G2, the present strain agrees more closely with *S. atrofaciens* in morphology and color of the growth and mycelium on various media, especially on glucose-asparagine agar and tyrosine agar, soluble pigment on starch-inorganic salts agar, liquefaction of calcium malate, hydrolysis of starch and peptonization and coagulation of skimmed milk. Thus, strain No. M590-G2 can be identified as *S. atrofaciens*.

Since the Streptomyces are easily mutatable naturally or artificially, *S. atrofaciens* No. M590-G2 in the present invention includes the typical strain described above and all natural and artificial variants and mutants thereof. That is, *S. atrofaciens* No. M590-G2 of the present invention includes all strains producing macracidmycin. As with the known antibiotics it is anticipated that higher production of macracidmycin can be achieved by the selection of highly productive strains after single colony selection, by the treatment of a macracidmycin-producing strain with various mutagens, or by the genetic procedures of transduction, transformation or recombination.

the source of nitrogen, an organic material such as peptone, meat extract, yeast extract, soybean meal, fish meal, malt extract, corn steep liquor, cooton seed meal, hydrolyzed protein substances, distiller's solubles and inorganic sources of nitrogen such as urea, nitrates and ammonium salts, e.g. ammonium sulfate, and other inorganic salts such as sodium chloride, potassium chloride, potassium phosphate, magnesium sulfate, calcium carbonate and trace amounts of heavy metal salts such as copper, manganese, iron, zinc and the like. In aerated submerged culture an antifoam such as liquid paraffin, soybean oil, fatty oils or silicone is used.

Culturing temperatures are usually 24° to 35° C., the most preferred range of temperature being 25° to 29° C. The pH of the culture medium ranges from 6 to 8.

When the fermentation was carried out at 27° C. with shaking using one of the suitable media at pH 7.2, i.e. glucose 1.0%, starch 1.0%, partially hydrolyzed soybean meal (Prorich) 1.5%, $KH_2PO_4$ 0.1%, $MgSO_4 \cdot 7H_2O$ 0.1%, NaCl 0.3%, $Cu^{++}$, $Fe^{++}$ and $Zn^{++}$ 2 ppm each, the pH of the medium dropped to 6.0 to 6.5 in 24 hours and the growth of mycelium increased rapidly at 48 hours after the inoculation. Thereafter, pH rose to 7.2 to 8.0 on 4 to 5 days and anti-Ehrlich carcinoma activity reached a maximum.

Macracidmycin exists mainly in the liquid part of the fermented broth after separation of the solid part by conventional filtration, centrifugation or other methods. Among the separation methods for macracidmycin, the effective ones are to salt out macracidmycin from aqueous solution, more particularly from a concentrated solution, by adding ammonium sulfate, sodium sulfate, etc., and to precipitate it by adding zinc chloride, by precipitation at pH 3 to 5, or by the addition of methanol, ethanol, acetone, etc.

The most effective method of purification is that in which macracidmycin is precipitated by by specially adding a proper amount of a saturated aqueous solution or powder of ammonium sulfate, and then dialyzed by using semipermeable membrane such as a cellophane tube to remove ammonium sulfate and low molecular weight impurities. For the same effect, gel-filtration agents, e.g. Sephadex G25 to G200, Sepharose 4B and 6B (Pharmacia Fine Chemicals AB, Uppsala, Sweden), Bio-Gel A1.5m (Bio Rad Co.), and ultrafilters, e.g. Dia-Filter (Nippon Vacuum Co., Tokyo) and Mullipore filter (Millipore CO., U.S.A.) etc. can be used to isolate macracidmycin from the active fractions effectively. Preferred gel-filtration agents include the carboxymethyl substituted cross-linked dextran gels described in columns 3 and 4 of U.S. Pat. No. 3,819,836.

After several repetitions of salting-out, isoelectric precipitation and dialysis, crude macramidmycin is obtained as a brown powder by evaporation under vacuum and lyophilization of the solution containing macracidmycin.

The crude macracidmycin includes two fractions possessing anti-Ehrlich carcinoma activity at pH 3.2 and 6.0 on an LKB8101 electrofocusing column (LKB-Produkter AB, Sweden) using carrier ampholite pH 3 to 10. When the crude macracidmycin was analyzed by gel-filtration using Bio-Gel A1.5m (50 to 100 mesh, Bio Rad Lab.) equilibrated with 0.05M Tris-HCl buffer containing 0.001M EDTA and 0.05M mercaptoethanol, three major peaks cytotoxic on Ehrlich carcinoma cell-containing agar plate, which were named FI, FII and FIII, were observed. Comparing the antitumor activity of FI, FII and FIII, and demonstrating the relationship of antitumor activity in vivo (in mice) and cytotoxicity in vitro (in culture), it was found that the antitumor activity in mice related closely to the cytotoxicity against Ehrlich carcinoma cells on the plate containing calf serum, and FIII fraction inhibited the growth of Ehrlich carcinoma in mice specifically as follows:

Relationship of Antitumor Activity of Active Fractions From Gel-filtration

| Fractions | Growth inhibition of Ehrlich Ascites cells | | |
|---|---|---|---|
| | On agar plate containing calf serum (15%) | On agar plate without serum | In mice |
| FI | ± | ++ | + |
| FII | − | +++ | − |
| FIII | +++ | + | +++ |

− no effect
± slight inhibitory effect
+ inhibitory effect
++ moderate inhibitory effect
+++ strong inhibitory effect Assay of antitumor activity:

1. Antitumor activity against Ehrlich ascites carcinoma in mice; Ehrlich ascites carcinoma were inoculated by intraperitoneal injection of 0.5 ml. aliquots containing $2 \times 10^6$ cells in 20 to 22 gram dd mice. 0.2 Ml. of macracidmycin-containing solution was injected intraperitoneally once daily for 10 days consecutively from 24 hours after the inoculation.

2. Cytotoxicity against Ehrlich ascites cells on agar plate; Ehrlich ascites carcinoma cells were harvested from ascites of dd mice on 7 to 10 days after inoculation by intraperitoneal injection of $2 \times 10^6$ cells, and rinsed three times with phosphate buffered saline (NaCl 8g. KCl 0.2 g., $KH_2PO_4$ 0.2 g., $K_2HPO_4$ 1.15 g., water 1,000 ml.), and resulting cells poured into Hanks agar medium (DIFCO agar 10 g., NaCl 8 g., KCl 0.4 g., $CaCl_2$ 0.14 g., $MgCl_2$ 0.1 g., $Na_{0.14}$ g., $MgCl_2$ $2HPO_4$ 0.06 g., $KH_2PO_4$ 0.06 g., $MgSO_4$ 0.1 g., glucose 1.0 g., phenol red 0.006 g. in 1,000 ml. of water) at the concentration of $2.5 \times 10^6$ cells/ml. and allowed to solidify. Paper disks were dipped in the test solutions containing macracidmycin and placed on the agar surface. After plates were incubated at 37° C. for 18 to 20 hours, paper disks were removed and the agar surface was flooded with 0.016% solution (calf serum: phosphate buffered saline = 1:1) of 2,6-dichlorophenol-indophenol and then allowed to stain for 1 hour at 37° C. Under these conditions the viable cells reduced the dye while the dead cells did not. The diameters of the blue zones of toxicity were measured. On the other hand, the cytotoxicity against Ehrlich ascites carcinoma in the presence of calf serum was determined using the same medium supplemented with 15% calf serum and the same conditions as described above.

Another useful purification process is the use of ion exchangers capable of adsorbing macracidmycin weakly which are DEAE-cellulose, ECTEOLA-cellulose, CM-Sephadex, CM-cellulose, SP-Sephadex. To obtain pure and highly remarkable antitumor fraction, the crude macracidmycin is purified by ion exchange chromatography combined with at least one or more process selected from the method of gel-filtration, salting-out, isoelectric precipitation, electrophoresis, electrofocusing, ultrafiltration, etc.

For example, when crude macracidmycin solution was subjected to a ECTEOLA-cellulose column and then was eluted with 0.02 M acetate or 0.02 M phosphate bufer (pH 6.2) increasing the sodium chloride concentration from 0.01 M to 0.1 M stepwise, active fraction FIII was eluted at 0.02 M of sodium chloride concentration and found to be free from a large amount of impure protein and high molecular substances. A small amount of impurities such as inorganic salts, high molecular substances and organic materials in FIII fraction were further removed completely by means of CM-Sephadex C-50 column chromatography using 0.01 M acetate buffer (pH 6.2), Sephadex G100 gel-filtration and dialysis. The resulting solution of pure macracidmycin can be stored in cold and frozen states, and can also be freeze-dried alone or with at least one stabilizer selected from serum albumin, globulin, gelatin, glycerol, sugars, amino acids, etc.

Figure 1:
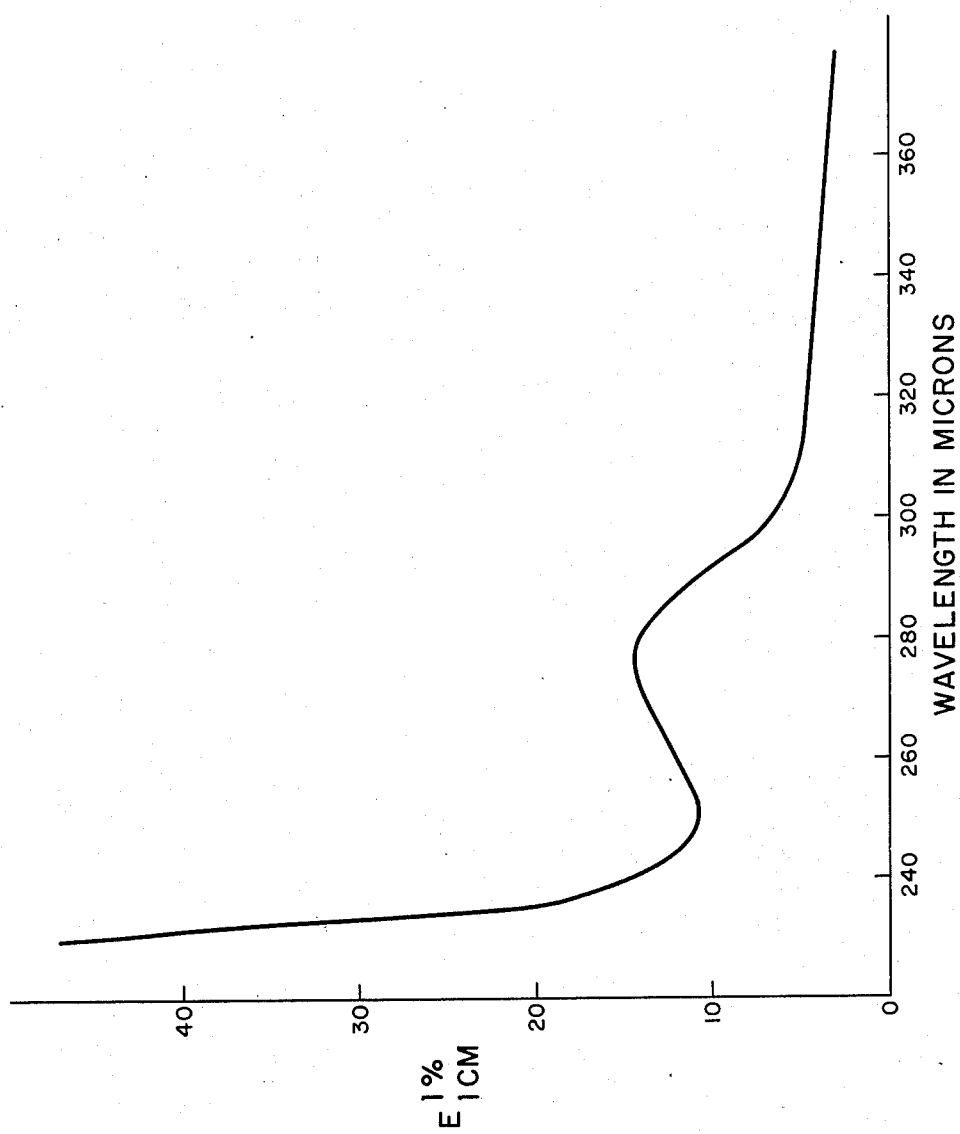
FIG. 1 shows ultraviolet absorption spectrum of macracidmycin in H$_2$O.

The macracidmycin obtained by a combination of the various above-mentioned methods, and described in the examples below was demonstrated to be pure and uniform by single band in polyacrylamide disk electrophoresis, symmetrical elution peak in column chromatography, and single peak on electofocusing using carrier ampholite, pH 5 to 7, and has the following properties:

1. Macracidmycin is a weakly acidic amorphous white powder rapidly soluble in water but substantially insoluble in organic solvents. The isoelectric point of macracidmycin is pH 6.0.
2. Molecular weight by means of gel filtration: 35,000 to 38,000.
3. The melting point is not clear but it decomposed by carbonization. 4. The ultraviolet absorption spectrum of macracidmycin in an aqueous solution and its infra-red absorption spectrum are as presented in FIGS. 1 and 2, respectively.
5. Macracidmycin is biuret, ninhydrin, Folin-Lowry and Sakaguchi positive, and phenol-$H_2SO_4$, Elson-Morgan and anthrone negative.
6. when it is subjected to hydrolysis in a sealed tube with 6 N hydrohloric acid at 110° C. for 20 hours, aspartic acid (8), threonine (7), serine (8), proline (2), glycine (16), glutamic acid (7), alanine (10), valine (4), isoleucine (2), leucine (4), tyrosine (2), phenylalanine (2) histidine (1), lysine (3), ammonia (16), arginine (2) and an unknown amino acid between histidine and lysine are determined to be present in the hydrolysate by using an amino acid autoanalyzer. The numbers in parenthesis mean the molar ratio of these amino acids. However, cystine and methionine were not detected therein.
7. Macracidmycin is stable to proteases such as trypsin and pepsin.
8. Macracidmycin has no enzyme activity such as is exhibited by proteases at pH 5, 7 and 10 and by phospholipases A, C and D.
9. Macracidmycin tends to be relatively stable at acidic and neutral pH (pH 6 to 10) and is unstable in alkali.
10. The activity of macracidmycin solution is rapidly decreased over 40° C. but is stable at 30° C.
11. Hemolysis: Hemolytic to sheep erythrocytes at 100 mcg./ml. of macracidmycin.
12. No antimicrobial activity against various gram positive and negative bacteria, Streptomyces, fungi, yeasts and mycoplasma was observed at a concentration of 100 mcg./ml. of macracidmycin by the agar dilution method.
13. Cytotoxic and cytolytic effects on cultured mammalian tumor cells: A characteristic of macracidmycin is that it, in contrast to its lack of inhibition of the growth of microorganisms at high concentrations, inhibits completely the growth of HeLa $S_3$, L1210 and L5178Y cells in culture at an extremely low concentration of 0.5 to 2 mcg./ml., and various cultured tumor cells exposed to the low concentration of macracidmycin for a short period (2 to 5 minutes) swell rapidly and finally lyse out following leakage of intracellular pool of amino acids and nucleotides. Protein and nucleic acid biosyntheses of L1210 and Ehrlich ascites cells are inhibited over 50% at 10 mcg./ml. of macracidmycin in the medium.
14. Antitumor effects: Furthermore, its antitumor action can be most significantly demonstrated in experimental tumors in mice. For example, when dd mice weighing 18 to 20 grams are inoculated with $2 \times 10^6$ cells of Ehrlich carcinoma cells intraperitoneally and macracidmycin is administered intraperitoneally once daily for 10 days consecutively 24 hours after the inoculation, in a wide range of doses, 50 mcg./kg. to 1.5 mg./kg. of body weight, macracidmycin distinctly suppressed the accumulation of abdominal dropsy without causing toxicity to mice. At doses of 1.0, 0.5 and 0.25 mg./kg., all of the treated mice fully recovered and lived.
15. Toxicity: $LD_{50}$ of single injection of macracidmycin is 8 to 10 mg./kg. intraperitoneally, and 1 to 1.5 mg./kg. intravenously in dd mice.
16. Macracidmycin has virucidal action on vaccinia virus; 50% inactivation at 50 mcg./ml., and 1 mcg./ml. of this antibiotic inhibits 50% of the growth of vaccinia virus in HeLa cells, while bacteriophages of E. coli are resistant to this antibiotic.

Among known high molecular weight antitumor substances enomycin, actinocarcin, peptimycin, sanitamycin, phenomycin and lymphomycin are non-dialyzable peptides having antitumor activity but no antimicrobial action.

Basic peptides phenomycin, enomycin, lymphomycin, peptimycin and actinocarcin, are different from the weakly acidic peptide, macracidmycin, in the properties of molecular weight, proteinous nature and amino acid composition. Sanitamycin is most similar to macracidmycin in acidic peptide and molecular weight, but differed from its isoelectric point and selective inhibition on protein synthesis of Ehrlich carcinoma cells. Thus macracidmycin is clearly differentiated from the above antibiotics as the above-stated properties. It is verified that this product is a new substance discovered by the present inventors and is a useful substance for animals.

Among known antibiotics, enomycin, phenomycin, actinogan, actinocarcin, largomycin, sanitamycin, and lymphomycin are non-dialyzable polypeptides having antitumor activity without antimicrobial action. Macracidmycin is clearly differentiated from the above antibiotics as the above-stated properties. It is verified that this product is a new substance discovered by the present inventors and is a useful substance.

Actual examples for the production and purification of macracidmycin are described below. The following examples are merely illustrative and it should be evident to technical experts that macracidmycin can be obtained by different, modified or combined means, even though not actually described herein, and such different or modified means are considered within the scope of the claim of this invention, since various characteristics of the active substance have been described. Therefore, it should be understood that our invention is not limited to these examples.

DESCRIPTION OF THE PREFERRED EMBODIMENTS

Example 1

A medium (50 ml.) consisting of glucose 1%, starch 1%, partially hydrolyzed soybean meal (Prorich) 1.5%, $KH_2PO_4$ 0.1%, $MgSO_4$ 0.1%, NaCl 0.3%, $Cu^{++}$ 7ppm., $Fe^{++}$ 1ppm., $Mn^{++}$ 8ppm and $Zn^{++}$ 2ppm. (pH 7.2) was placed in a Sakaguchi-shaking flask of 500 ml. and sterilized at 120° C. for 20 minutes. To this sterilized medium, Streptomyces atrofaciens No. M590-G2 was inoculated from an agar slant culture by platinum loop. Incubation proceeded on a reciprocal shaker (130 rpm) for 2 days at 27° to 29° C. An inoculum of 2.5 ml. of above seed culture was transferred to 250 fermentation flasks each containing 120 ml. of the same medium which was prepared as above. Fermentation was carried out at 27° C. for 5 days on a reciprocal shaker and 24 L of the broth was yielded. The broth obtained was filtered at pH 7.4 and filtrate contained 940 μg./ml. of macracidmycin. The filtrate was adjusted to pH 6.0 with 1 N hydrochloric acid, and 9.1 kg. of ammonium sulfate was added, stirred frequently and let stand at 4° C. for 18 hours. The precipitate containing macracidmycin was collected by centrifugation and dissolved in 1000 ml. of 0.01M Tris-HCl buffer (pH 7.0). Then, insoluble materials were centrifuged off and an equal volume of 100% saturated ammonium sulfate solution was added to the supernatant and let stand at 4° C. for 20 hours. The resulting precipitate containing macracidmycin was dissolved in 650 ml. of 0.01 M Tris-HCl buffer (pH 7.0) and placed into cellophane tube for dialysis against the same buffer at 4° C. for 18 hours. The inner solution containing 425 mg. of macracidmycin was applied to a column 10 cm. in diameter and 45 cm. in length filled with ECTEOLA-cellulose, and eluted with 0.02 M phosphate buffer (pH 6.2). The initial 2 L of eluate was discarded and an active fraction of 1000 ml. was concentrated to 80 ml. by an ultrafilter (Dia-Filter G10). The concentrate contained 285 mg. of macracidmycin and was applied to a column 7 cm. in diameter and 35 cm. in length filled with a gel-filtration agent (CM-Sephadex C-50), and then chromatographed with 0.02 M acetate buffer (pH 6.2). The active fraction of 260 ml. was concentrated to 70 ml. which contained 117 mg. of macracidmycin, by an ultrafilter (Dia-Filter G10) and was lyophilized. The crude macracidmycin powder (235 mg.) so obtained was shown to be about 50% pure.

Example 2

The crude powder (235 mg.) obtained in Example 1 was dissolved in 50 ml. of deionized water and applied to a column 5 cm. in diameter and 55 cm. in length filled with Sephadex G-100. The active fraction of 150 ml. was concentrated to 40 ml. which contained 46 mg. of macracidmycin, by an ultrafilter (Dia-Filter G-10). 20 Ml. of pure macracidmycin solution was mixed with 20 ml. of 0.02 M phosphate buffer containing 0.1 M NaCl and kept at 4° C. Another 20 ml. of this solution was dialyzed against deionized water at 4° C. for 20 hours and then lyophilized and 10.5 mg. of pure macracidmycin was obtained. Pure macracidmycin thus obtained inhibited completely the growth of Ehrlich ascites carcinoma in dd mice at the dose of 78 μg./kg./day by intraperitoneal administration.

We claim:
1. The process for producing antibiotic macracidmycin which comprises culturing a macracidmycin-producing strain of *Streptomyces atrofaciens* having the identifying characteristics of A.T.C.C. 31104 under submerged aerobic conditions in a nutrient medium containing a carbon source and a nitrogenous nutrient until a substantial amount of macracidmycin is produced by said organism in said nutrient medium.
2. The process of claim 1 in which a macracidmycin-producing strain of *Streptomyces atrofaciens* having the identifying characteristics of *Streptomyces atrofaciens* A.T.C.C. 31104 is cultured in a nutrient medium at a temperature in the range of 24° to 35° C.
3. The process of claim 1 in which a macracidmycin-producing strain of *Streptomyces atrofaciens* having the identifying characteristics of *Streptomyces atrofaciens* A.T.C.C. 31104 is cultured in a nutrient medium at a temperature in the range of 25° to 29° C. with the pH from 6 to 8.
4. The process of claim 1 which includes the further step of recovering the macracidmycin from the culture medium.
5. The process of claim 4 in which the macracidmycin produced in the cultured broth is extracted and purified by a process which includes one process selected from the group consisting of salting-out, solvent precipitation, dialysis, ultrafiltration, isoelectric precipitation, gel filtration, electrophoresis, electrofocusing and adsorption followed by elution from an ion exchange resin.
6. The process of claim 1 in which the solution containing macracidmycin is stored in a cold or frozen state.
7. The process of claim 1 in which the solution containing macracidmycin is freeze dried.
8. The process of claim 1 in which the solution containing macracidmycin is freeze-dried after addition of one stabilizer selected from the group consisting of serum, serum albumin, serum globulin, casein, glycerol, gelatin, sugars and amino acids.
9. The antibiotic macracidmycin produced by the process of claim 1 which:
   a. is effective in inhibiting the growth of ascites forms of Ehrlich carcinoma and Sarcoma 180 in mice, and vaccinia virus in HeLa cells;
   b. can be isolated as a white amorphous powder;
   c. is soluble in water but substantially insoluble in organic solvents;
   d. exhibits an ultraviolet absorption maximum at 280 microns in aqueous solution;
   e. exhibits characteristic maxima in the infrared absorption spectrum at 3320, 3075; 2940, 1645, 1540, 1460, 1420, 1230 and 1070 $cm^{-1}$;
   f. gives positive Folin-Lowry, ninhydrin, Sakaguchi, and biuret reactions and negative Elson-Morgan and anthrone reactions;
   g. has an isoelectric point of pH 6.0;
   h. is a weakly acidic polypeptide having a high molecular weight for which a molecular weight of 35,000 to 38,000 is indicated by gel filtration; and
   i. gives upon acid hydrolysis the following amino acids (molar ratio): Aspartic acid(8), threonine(7), serine(8), glutamic acid(7), proline(2), glycine(16), alanine(10), valine(4), leucine(4), isoleucine(2), tyrosine(2), phenylalanine(2), histidine(1), lysine(3), arginine(2), ammonia(16) and an unknown amino acid between histidine and lysine on an amino acid analyzer.

* * * * *